US00PP08989P

United States Patent [19]

Filter et al.

[11] Patent Number: Plant 8,989

[45] Date of Patent: Nov. 29, 1994

[54] FILTER CLING PEACH

[76] Inventors: Timothy A. Filter; Phillip W. Filter; Jerry P. Filter; James R. Filter, all of 1010 Morse Rd., Live Oak, Calif. 95953

[21] Appl. No.: 144,697

[22] Filed: Oct. 28, 1993

[51] Int. Cl.[5] ..... A01H 5/00

[52] U.S. Cl. ..... Plt./43.1

[58] Field of Search ..... Plt. 43.1

*Primary Examiner*—James R. Feyrer

*Attorney, Agent, or Firm*—Bernhard Kreten

[57] ABSTRACT

A peach tree which is of large size, open density, vigorous, hardy, upright to spreading-upright, vigorous upright shoots foliated with medium to large size, lanceolate leaves, having acuminate tips, irregular broad crenate margins, mostly globose and occasionally oval and reniform glands which are medium in size, and the stipules are average, light shiny green in color, darkening with age, and early-deciduous with most falling early in the season, blooms abundantly in season with other varieties of peach trees with a hardy, medium size bud which is conical in shape and remaining slightly cupped inwards even at full expansion, pale pink medium flowers, and a regular productive bearer of a heavy, well set crop of medium to large, uniform, somewhat variably formed, very early ripening canning clingstone fruit having light orange red to a darker lacquer red color skin with a light red blush covering 10 percent to 60 percent of the fruit surface varying from a washed pattern to a mottled and dappled spotted pattern, and bright yellow flesh, becoming slightly darker near the stone, and no red coloration is present under the skin surface. The fruit ripens substantially earlier than the earliest commercial variety presently grown, has excellent canned appearance and quality and may now be the earliest volume canning peach variety, allowing earlier opening of the canneries (by approximately two weeks), thus extending the canneries' season.

1 Drawing Sheet

DISCOVERY OF THE VARIETY

The present new and distinct variety of peach tree was first observed by the inventors in a commercial orchard of "Loadel" cling peach as a single mutated scaffold branch on a tree of "Loadel" peach growing on the "Loadel" topstock itself. The commerical orchard where the new variety was discovered is owned and operated by the inventors, and is known as "Filter Farms, Inc.". The inventors observed that the branch was substantially different than the parent "Loadel" and took particular note of its advanced branch maturity in relation to the parent "Loadel". Thus, the inventors realized that the branch was substantially different from the regular "Loadel" variety in that the new variety was approximately two weeks earlier in maturity. The inventors then propagated five new trees by budding onto Lovell seedling rootstock; which came true to type from the originally discovered limb sport of the new variety.

ASEXUAL REPRODUCTION OF THE VARIETY

A number of plants (five) of the present variety were asexually reproduced from bud wood obtained from the original mutated branch; by placing buds onto Lovell seedling rootstock, the work was performed by the inventors on their commercial orchard in Gridley, Calif. (23 Hurlburt Lane, Gridley, Calif.). These propagated trees first fruited in 1989 and were observed then and in subsequent years to be clones of the originally discovered branch mutation, being identical to the original mutation scaffold in every distinguishing characteristic.

SUMMARY OF THE VARIETY

The present variety of peach tree is, characteristically, of large size, excellent vigor, with an upright to upright-spreading structure. The tree's truck is relatively thick in diameter with rough bark texture. The tree is foliated in an abundant quantity with lanceolate leaves, having acuminate tips. The margins are irregular, and formed with medium sized broad crenations being only slightly undulate. The leaves are generally medium to large in size on vigorous upright shoots. The leaf stipules are average in size, light shiny green in color, darkening with age. These stipules are early-deciduous with most stipules falling early in the season. The tree blooms at the same time as other commercial cling peach varieties with grey-brown flowers from 18 to 22 mm. in diameter when fully expanded. The bloom quantity is abundant, being heavier than the parent "Loadel" on the original tree. From 2–3 flowers are present per node. The tree is productive and a regular bearer of a heavy well set crop of medium to large uniform sized peaches of the clingstone variety having bright yellow, firm, fine non-melting textured flesh with no red coloration present in the flesh or near the stone. The new fruit of the variety is slightly larger in size than the "Loadel". The skin is of average thickenss and moderately pubescent with a uniform covering of light greyish color, medium length hairs. The skin is neutral in acidity and tenacious to the flesh at commercial maturity. The fruit has a light red blush that can cover from 10 percent to as much as 60 percent of the fruit surface. Most commonly, blush percentages is in the 15 percent to 30 percent range. Blush form varies from a washed pattern to a mottled and dappled spotted pattern. Some blush striping is present in some instances. Ground color is golden yellow and is present over 40 percent to as much as 90 percent of the fruit surface. The fruit ripens evenly.

The tree is a vigorous grower, and upright to upright-spreading in growth characteristics. The tree is productive and a regular bearer. The tree is hardy under typical Sacramento Valley climatic conditions. The truck is relatively thick in diameter with rough surface texture exhibiting moderate scarfskin. The subject tree was pruned to a standard open-vase shaped form. Pollination studies have not been done, however, pollen production is abundant and the new variety is self fertile.

The tree blooms in early to mid March (Mar. 11th in 1993) in the Butte County. The new variety blooms at the same time as other commercial cling peach varieties, including the "Loadel". The tree blooms abundantly, with the number of flowers per node ranging from 2 to 3 (most frequently 2 are present). Flower buds are of medium size. Bud form is conic and relatively free from the stem. The bud surface character is very pubescent. The new variety has a more dense bloom than the "Loadel" variety. The fruit of the new variety matures approximately 2 weeks earlier than the "Loadel" variety, with the first pick on Jun. 25th through Jul. 1st (1992). The "Loadel" ripens from July 10th through July 15th. The fruit of the new variety is slightly larger in size, exhibits more external red blush and darker yellow interior flesh coloration than the "Loadel" variety.

The new variety is an extra early season, non-melting yellow fleshed canning clingstone peach, with a small stone, excellent fruit size and good flavor. The new variety closely resembles the early ripening cling peach variety "Loadel". However, the new variety is distinctly earlier in maturity than "Loadel". Additionally, the new variety enjoys a greater bloom density and somewhat larger fruit than the "Loadel" variety. When canned, the new variety is of high quality and appearance, being very similar to the "Loadel" when canned. Currently, the "Loadel" variety is the earliest volume canning peach variety used by commercial canneries. The discovery and eventual commercialization of the new cling peach variety is of substantial value to the canning peach industry because it will allow for earlier opening of the canneries (by two weeks) and for more efficient utilization of cannery facilities due to the extended season.

BRIEF DESCRIPTION OF THE DRAWING

The drawing is an illustration, by photographic reproduction in color, depicting fruit of the variety. Taken clockwise from the lower left-hand corner, there is depicted: a whole fruit taken from a lateral view, a whole fruit showing its suture, a whole fruit showing its apex, a whole fruit showing its base, a fruit cut along its side taken from a lateral view and showing the flesh of the fruit. The drawing also depicts foliage of the variety, taken clockwise from the upper right-hand corner: a portion of the current season's growth with the leaves attached and showing the top face, and two leaves of the current season's growth showing the bottom face.

DESCRIPTION OF THE VARIETY

The following is a detailed description of the variety of peach tree growing under the ecological condition prevailing near Gridley, Butte County, Calif. Color references are to the Maerz and Paul *Dictionary of Colors,* first edition 1930, except where terminology having generally accepted meaning is employed.

Tree:

*Size.*—Medium: 15 ft. height; 10 ft. width.

*Density.*—Open (determined by pruning).

*Vigor.*—Vigorous, hardy.

*Age.*—6 years.

*Rootstock.*—Lovell.

Trunk:

*Size.*—Medium: 12" to 14" diameter (5 year old tree).

*Texture.*—Rough, exhibiting moderate scarfskin.

*Lenticels.*—Numerous (abundant), oval shaped bark lenticels; 4.0 to 7.0 mm. width; 1.5 to 2.0 mm. height.

*Color.*—Kermanshah brown (7-C-10).

Branches:

*Size.*—Medium (average).

*Texture.*—Generally glabrous, especially with respect to current season's shoots.

*Branching habit.*—Upright to Upright-spreading.

*Lenticels.*—Very few lenticels are present on the current season's shoots.

*Color.*—The shoots are light green (18-K-6) with exterior shoots usually tinged with red where exposed to direct sunlight. Mature branches are medium brown (15-A-12) burnt umber).

Foliage:

*Quantity.*—Abundant: internode length (between leaf nodes) is normal ranging from 17 to 26 mm. on medium sized hanger fruit wood.

Leaves:

*Size.*—Medium to large.

*Shape.*—Lanceolate. The leaf tip form is acuminate with the apex often twisted sideways.

*Length.*—16.0 to 17.5 cm. (including the petiole).

*Width.*—13.8 to 14.6 cm.

*Thickness.*—Average.

*Texture.*—Average (normal).

*Margin.*—Only slightly undulate. The form is crenate, at times doubly so, with medium sized broad crenations. The crenations are somewhat irregular with variations in size and regularity of spacing.

*Petiole.*—10 to 13 mm. in length. 1.5 to 2.0 mm. in thickness. Light green (18-J-6) with a darker green within the petiole groove (20-J-7).

*Glands.*—Medium in size and variable in form. Most frequently globose, but occasional oval and reniform types can be present. Gland numbers are variable, from 1 to 5 glands can be present. Most frequently, 2 to 4 stalked globose glands are present on the petiole, arising out of the top of the ridges subtending the petiole groove and just below the base of the leaf blade. Another 1 or 2 variably formed glands can be present on the base of the leaf blade. Gland position is variable, but most frequently the stalked petiole glands are alternate in position. Color on young leaves is shiny green (18-L-6), becoming darker with age.

*Stipules.*—Average in size. 12 to 14 mm. in length. Linear lanceolate form and margins are serrate. Young stipules are light shiny green (19-L-5), darkening with age. Early deciduous.

*Color.*—Upper leaf surface — dark green (23-L-8). Lower leaf surface — light grey-green (22-I-5). Young shoot tip — bright green-yellow (19-L-6).

*Quantity.*—Abundant.

*Internode length.*—Normal, ranging from 17 to 26 mm. on medium sized hanger fruit wood.

Flower bud:

*Quality.*—Hardy.

*Size.*—Medium.

*Shape.*—Conic, relatively free from the stem.

*Surface.*—Very pubescent.

*Color.*—Grey-brown (7-A-10) (new cocoa brown).

*Condition.*—Dormant.

Flowers:

*Size.*—Medium: fully expanded 18 to 22 mm.

*Color.*—Pale pink (1-F-7) in the central portion of the petal, with darker pink (1-G-2) coloration on the petal margins and darker yet (1-J-3) basally on the petal claw.

*Pedicel.*—Average length, from 2.0 to 2.5 mm. Average thickness, about 1.5 mm. Shiny green color (18-L-5). Glabrous surface.

*Nectaries.*—Orange (9-C-12) becoming slightly duller with age.

*Calyx.*—Glabrous and rugose surface. Greenish (18-L-5) basally; overlain with maroon (7-H-4) coloration and speckling of the same color on its upper surface.

Petals:

*Size.*—Medium: 11 to 13 mm. length; 7 to 9 mm. width.

*Form.*—Variable: from slightly ovate to oval very slightly obovate. Petal number is five.

*Claw form.*—Short and tapered basally.

*Margins.*—Moderately undulate and usually cupped inwards.

*Apex.*—Variable, but usually somewhat domed.

Bloom:

*Quantity.*—Abundant: from 2 to 3 flowers per node, most frequently 2.

*Date of full bloom.*—March 11th.

*Anthers.*—Average size. Bright red (3-L-10 goya red) ventrally and light tan (10-I-4 pond lily) dorsally.

*Stamens.*—Variable 9 to 13 mm. in length. The longest stamens are about equal in length to the pistil. Filament color is light pink (1-B-1) darkening with age to a dark rose (5-H-4).

*Pollen.*—Abundant. Yellow-gold (10-L-4 chrome yellow).

*Pistil.*—14 to 16 mm. in length (including the ovary). Pale yellow-green (18-E-2). Pubescent surface.

Fruit:

*Maturity.*—When described — Full commercial maturity. Date of first picking — Jun. 25, 1992. Date of last picking — Jul. 1, 1992.

*Size.*—Medium to large, cheek diameter 61 to 68 mm., suture diameter 61 to 67 mm. and axial diameter 57 to 67 mm.

*Uniformity.*—Very uniform sizing.

*Form.*—Somewhat variable; most frequently ovate to occasionally oblate laterally; most frequently globose to occasionally oval apically; fruit symmetry is fully symmetrical to, at times, slightly asymmetrical.

*Suture.*—Extends continuously from base to apex and is relatively deep, being slightly deeper at times over the basal shoulder. Suture line extends past the apex 8 to 12 mm. on to the dorsal side of the apex. No stitching or callousing is present. A narrow golden-yellow (9-L-6) suture stripe ranging from 2 to 3 mm. in width can be present when the suture is overlain with blush coloration. When the suture area is underlain with yellow ground color (9-L-6) the suture stripe is not evident.

*Ventral surface.*—Generally smooth in outline, but substantially lipped.

*Cavity.*—Medium: 25 to 31 mm. width, 27 to 34 mm. length and 12 to 15 mm. depth. Generally oval form. Shoulders frequently have indentation marks where the attached branch has pressed into the fruit shoulder.

*Base.*—Slightly truncate. The base angle is variable but most frequently is at a right angle to the fruit axis.

*Apex.*—Variable, rounded to slightly raised. Pistil point is variable in height, at time located below the apical shoulders and recessed into the suture groove, at other times located above the apical shoulders on the suture groove, but in a raised position. Pistil point is most frequently oblique.

*Stem.*—Medium: 10 to 12 mm. in length. Thickness ranges from 2 to 3 mm. Light green (21-L-5) grass green) to a light brown (14-L-7 old bronze).

Skin:

*Thickness.*—Medium to slightly thicker than average.

*Surface.*—Moderately pubescent with a uniform covering of light greyish, medium length hairs over the entire fruit surface.

*Character.*—Neutral in acidic and tenacious to the flesh at commercial maturity.

*Tendency to crack.*—No cracking.

*Color.*—Light orange-red (2-J-11 brigand red) to a darker red (4-K-11 lacquer red). The fruit has a light red blush that can cover from 10 percent to 60 percent of the fruit surface. Most commonly, blush percentage is in the 15 percent to 30 percent range. Blush form varies from a washed pattern to a mottled and dappled spotted pattern. Some blush striping can also be present. Ground color is present over 40 percent to 90 percent of the fruit surface. Ground color is a golden yellow (9-L-6 golden glow).

Flesh:

*Color.*—Bright yellow (9-L-4 sunflower). The flesh is slightly darker near the stone (10-L-5 primuline yellow). No red coloration is present in the flesh or near the stone.

*Juice.*—Juicy at maturity.

*Texture.*—Firm, fine within the non-melting category of flesh texture. A moderate number of short, light colored, tender fibers are present throughout the flesh.

*Ripening.*—Ripens evenly.

*Flavor.*—Sweet, well balanced rich pleasant flavor.

*Aroma.*—Moderate, pleasant.

*Eating quality.*—Very good.

Stone:

*Adherence to flesh.*—Full clingstone.

*Size.*—Small. 27 to 30 mm. length, 21 to 22 mm. width and 15 to 18 mm. thickness.

*Form.*—Variable, from most frequently oval to at times ovate.

*Fibers.*—Numerous short, light colored fibers, attached over the stone surface.

*Hilum.*—Small and oval in form. Well defined by a relatively thick and raised collar.

*Base.*—Rounded to slightly truncate. Base angle is oblique to the stone axis, shorter on the dorsal suture side.

*Apex.*—Generally rounded, with a short dentate tip.

*Sides.*—Variable, from unequal to nearly equal.

*Dorsal edge.*—Relatively broad with a moderately deep groove present from the base to within 7 to 10 mm. of the apex. The groove narrows and the apical shoulder becomes somewhat eroded near the apex. The groove is bordered on each side by a low ridge which is cut by several cross grooves.

*Ventral edge.*—Narrow to medium 4 to 5 mm. thickness at mid-stone. Several low wings present along the edge, coalesced together and converge apically. The coalesced wings are very prominent at the basal shoulder forming a keel-like structure that protrudes out 4 to 5 mm. from the body of the stone.

*Surface.*—Coarsely grooved laterally across the apical shoulders, 11 to 15 mm. down from the apex. Sides are moderately pitted with medium sized oval to globose pits. Numerous small grooves are present near the base of the stone, converging basally.

*Color.*—Dry stone color is a light chamois-tan (11-G-6).

*Tendency to split.*—No tendency to split observed.

Use: Canning peach industry.

Canning quality: Excellent.

Resistance to insects: No unusual susceptibilities noted.

Resistance to disease: No unusual susceptibilities noted.

Although this novel variety of peach tree possesses the described characteristics under the ecological conditions at Gridley, Butte County, Calif., it is to be understood that variation in these characteristics incident to differing climatic and soil condition and cultural practices are anticipated.

We claim:

1. A new and distinct extra-early season variety of a clingstone peach tree having flesh of the yellow variety and substantially as herein shown and described, having firm, fine non-melting flesh texture, the fruit having a sweet, well balanced, rich flavor, being of medium to larger size, light orange-red to a darker lacquer red in color with a light red blush present from 10 percent to 60 percent of the fruit surface, and by having a desirable symmetrical shape, where the bloom density is greater, the fruit size is larger and the peach ripens substantially before other existing commercial varieties, typically in late June to early July and has an excellent appearance and quality when canned.

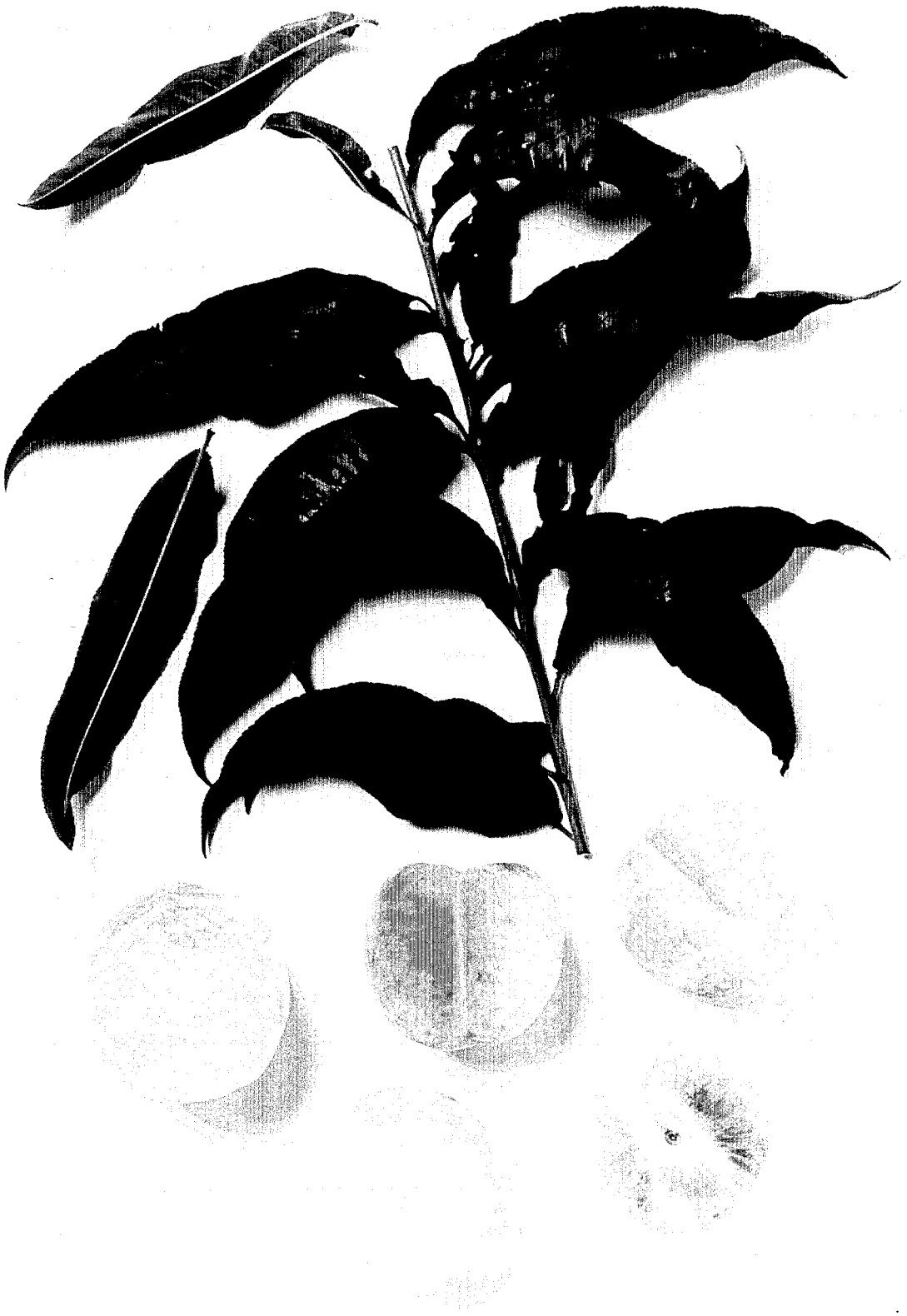

* * * * *